United States Patent [19]

Karaki et al.

[11] Patent Number: 4,977,544
[45] Date of Patent: Dec. 11, 1990

[54] ULTRASONIC MICROSCOPE

[75] Inventors: Koichi Karaki, Hino; Mitsugu Sakai; Yasuo Sasaki, both of Hachiooji, all of Japan

[73] Assignee: Olympus Optical Co., Ltd., Tokyo, Japan

[21] Appl. No.: 378,767

[22] Filed: Jul. 12, 1989

[30] Foreign Application Priority Data

Jul. 21, 1988 [JP]  Japan .................................. 63-182679

[51] Int. Cl.⁵ ....................... G01N 29/00; G01N 29/22
[52] U.S. Cl. .......................................... 367/7; 73/620; 73/634
[58] Field of Search ....................... 367/7; 73/606, 618, 73/620, 627, 634

[56] References Cited

U.S. PATENT DOCUMENTS 4,435,985  3/1984  Wickramcsinghe .................. 73/606
4,706,185  11/1987  Karaki et al. ....................... 367/110

FOREIGN PATENT DOCUMENTS 57-194060  12/1982  Japan .
58-196453  11/1983  Japan .
59-44582   10/1984  Japan .
0231159    10/1987  Japan ..................................... 73/606

OTHER PUBLICATIONS

The Journal of Acoustic Society of America, vol. 67 (1980), pp. 1, 629-637-J. Heiserman et al.

*Primary Examiner*—Ian J. Lobo
*Attorney, Agent, or Firm*—Frishauf, Holtz, Goodman & Woodward

[57] ABSTRACT

An ultrasonic microscope includes a sample rod for supporting a sample and an acoustic lens positioned to face the sample. The lens is moved in two directions in a plane perpendicular to each other to scan the sample. During the scanning operation, the lens is also moved in a vertical direction so that the distance between the sample and acoustic lens is changed, by a piezoelectric actuator for supporting the lens.

20 Claims, 5 Drawing Sheets

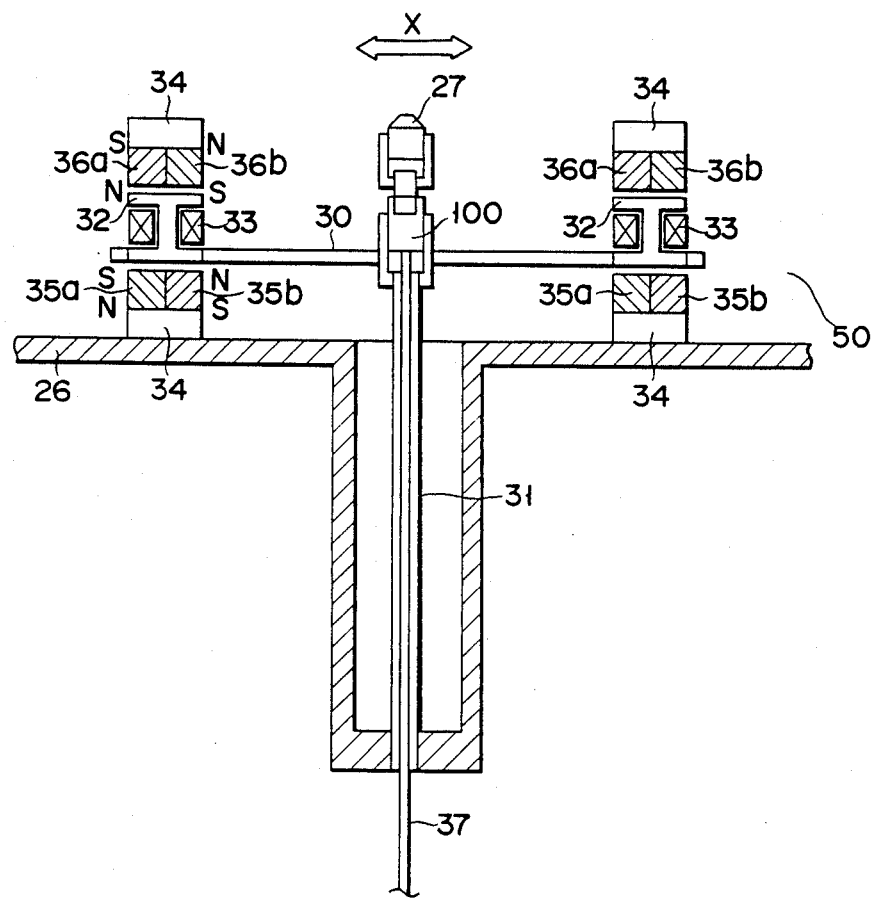
F I G. 2

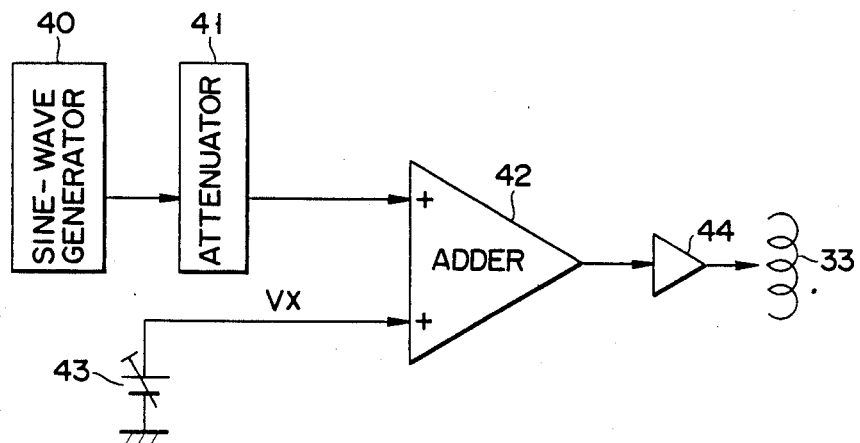
F I G. 3A
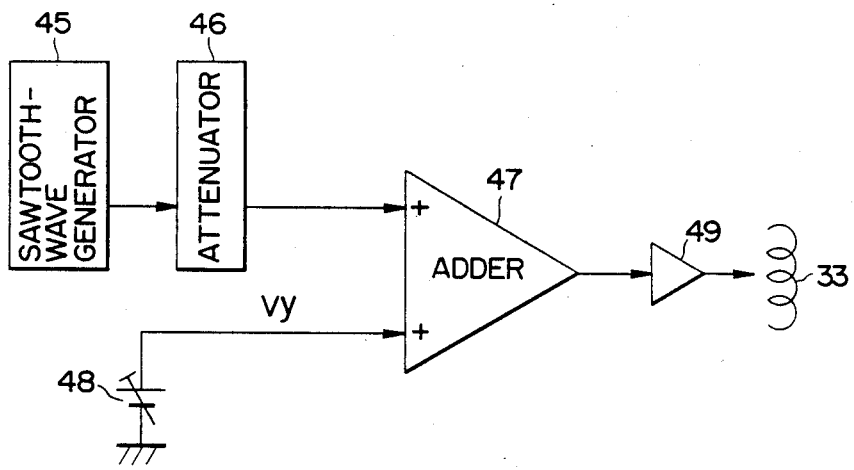
F I G. 3B

ULTRASONIC MICROSCOPE

BACKGROUND OF THE INVENTION

1. Field of the Invention

The present invention relates to an ultrasonic microscope having a focusing-coupling mechanism.

2. Description of the Related Art

Japanese Patent Publication No. 59-44582 and Janapanese Patent Disclosure No. 58-196453 disclose ultrasonic microscopes in which a sample is two-dimensionally scanned with an ultrasonic beam, and the waves transmitting through, or reflected from, the sample are processed to form an image for the sample.

Also, *the Journal of Acoustic Society of America, Vol.* 67 (1980),pp. 1,629-37 discloses a cryogenic ultrasonic microscope which can provide a high-resolution ultrasonic image. The cryogenic ultrasonic microscope has an acoustic lens. Cryogenic fluid is filled in the gap between the acoustic lens and a sample. The cryogenic fluid is, for example, liquid nitrogen, liquid argon, or liquid helium, which transmits sound more slowly and absorbs less than water.

These conventional ultrasonic microscopes have a focusing mechanism which moves a sample rod, coarsely and minutely, thereby moving a sample to a desired position. Because of the use of the focusing mechanism, the conventional microscope is disadvantageous in the following respects:

1. Since the sample rod is often detached from, and attached, to, the focusing mechanism to replace a sample by another, the rod must be easily detached from, and attached to, the mechanism. To facilitate the detaching and attaching of the rod, the microscopes need to have a complex mechanism for attaching and detaching the rod.

2. An O-ring is mounted on the upper end of the sample rod, thus providing a vacuum seal for the cryogenic fluid. Consequently, the upper end of the rod is not firmly sutured to the focusing mechanism, and it is difficult to for the focusing mechanism to move the sample to the desired position.

SUMMARY OF THE INVENTION

The object of the present invention is to provide an ultrasonic microscope having a mechanism which has a simple structure and can yet reliably move a sample to a desired position.

This object is achieved, in a microscope of the type having a sample rod extending into a container of cryogenic liquid, by supporting the acoustic lens in the cryogenic liquid and providing means for moving the lens to change the direction between lens and the sample, More particularly, the acoustic lens is supported on a base suspended from stays fixed to the container, and piezoelectric means are interposed either between the base and the lens, or between the base and the stays. A scanning system may be provided on the base for moving acoustic lens two dimensionally in a scanning plane at least substantially perpendicular to the one direction. Where individual piezoelectric actuators are provided on the stays, they may be individually driven to control the tilt of the scanning plane.

BRIEF DESCRIPTION OF THE DRAWINGS

FIG. 2 is an enlarged view of the acoustic lens and some other components of the microscope shown in FIG. 1;

FIGS. 3A and 3B are diagrams showing driver circuits for driving the acoustic lens in the x- and y-directions, respectively;

DETAILED DESCRIPTION OF THE PREFERRED EMBODIMENTS

Figure 1:
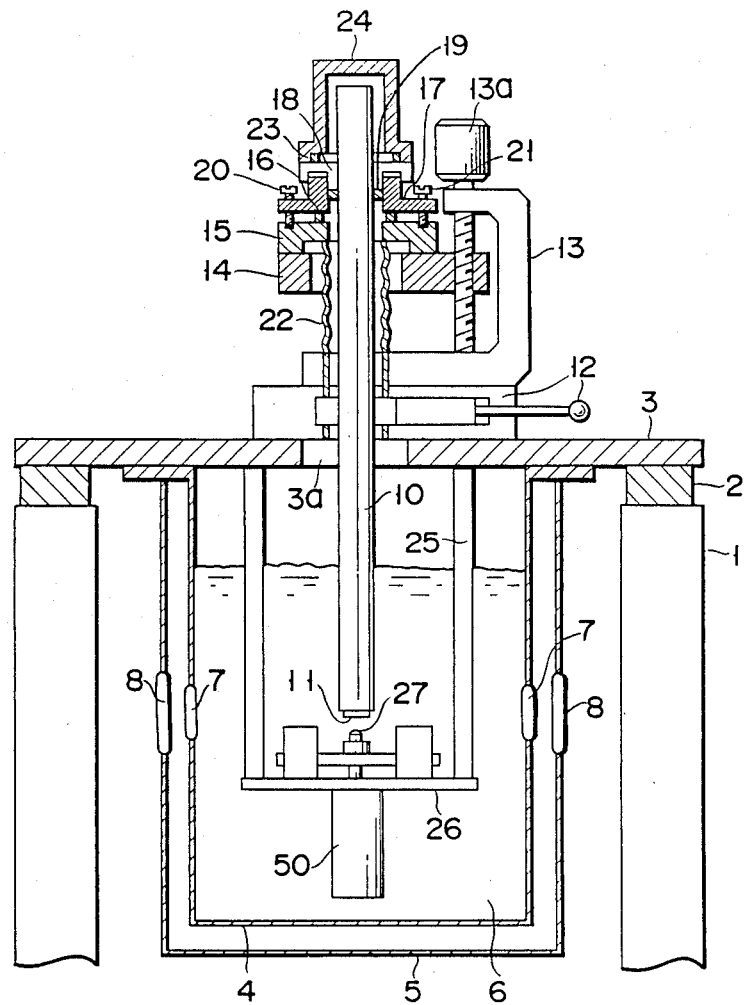
FIG. 1 is a schematic view showing an ultrasonic microscope according to a first embodiment of the invention.

FIG. 1 shows a cryogenic ultrasonic microscope according to the first embodiment of the present invention. As illustrated in FIG. 1, the ultrasonic microscope comprises a microscope body 1, an air damper 2 connected to the top of the body 1, and a base plate 3 mounted on the air damper 2 and extending horizontally mounted on microscope body 1. The microscope further comprises an adiabatic vessel 4 located in the body 1 and hermetically suspended from the plate 3, and a cover 5 also hermetically suspended from the plate 2 and surrounding the vessel 4. Hence, the vessel 4 and the cover 5 define an enclosed annular space. The vessel 4 contains liquid nitrogen 6 used as ultrasonic transmission medium. A vacuum is formed in the annular space in order to prevent the temperature of the liquid nitrogen 6 from rising. The vessel 4 and the cover 5 have windows 7 and 8, respectively, each made of a transparent plate, through which the inside of the vessel 4 can be seen.

The base plate 3 has central opening 3a. A sample rod 10, which is a stainless-steel pipe and may be tilted, may be vertically moved through this opening 3a so that its lower end portion can be immersed into and pulled out of the liquid nitrogen 6 in the adiabatic vessel 4. A sample 11 is attached to the lower end of the rod 10.

The ultrasonic microscope also comprises a gate valve 12 mounted on plate 3, and a micrometer head 13 mounted on the gate valve 13 and supporting a micrometer 13a. Both the valve 12 and the head 13 are arranged to allow the sample rod 10 to pass through them. When the rod 10 is removed from the microscope in order to detach the sample 11 from the rod 10 and to attach a new sample thereto, the valve 12 is closed to seal vessel 4.

A movable plate 14 is fastened to the spindle of the micrometer 13a. Hence, when the spindle of the micrometer 13a is rotated, the plate 14 is moved up or down, in the z-direction. A stationary block 15 is mounted on the movable plate 14. The plate 14 and the block 15 have coaxial holes, through which the upper portion of the sample rod 10 passes. Further, a movable block 17 is located above the block 15, with an O-ring 16 interposed between the blocks 15 and 17.

A sleeve 18 is set in engagement with the movable block 17 so that the sample rod 10 is supported by the inner periphery of the sleeve 18. An O-ring 19 is interposed between the rod 10 and the block 17. A pair of adjust screws 20 and 21, and another pair of adjust screws (not shown) are set in the vertical holes made in the movable block 17. When these screws are rotated, they change the inclination of the movable block 17 with respect to the stationary block 15, thereby adjusting the tilt of the sample rod 10, and ultimately adjusting the angles at which the sample 11 is inclined to an x-direction and a y-direction in a horizontal plane.

Flexible bellows 22 are stretched between the micrometer head 13 and the stationary block 15, surrounding the sample rod 10. A cover 24 is located above the sleeve 18, with an O-ring 23 interposed between it and the sleeve 18. The cover 24 covers that upper portion of the rod 10 which projects from the sleeve 18.

Several stays (for example four stays) 25 protrude vertically from the lower surface of the base plate 3 such that their lower portions can be immersed in the liquid nitrogen 6 contained in the adiabatic vessel 4. A nonmagnetic support base 26 is fixed to the lower end portions of stays 25, and extends horizontally. Acoustic lens 27 is mounted on base 26 and may be movably supported in the x- and y-directions by means of an elastic support mechanism 31 (FIG. 2). An electromagnetic drive mechanism (i.e., an X-Y scanner 50) is provided to drive the lens 27 in the x- and y-directions. The stays 25 are formed of a material whose coefficient of thermal expansion is substantially equal to that of sample rod 10.

FIG. 2 shows arrangements of the elastic support mechanism 31 and the electromagnetic drive mechanism for the acoustic lens 27. The lens 27 is supported on the center of a cross-shaped movable member 30 which is formed of a nonmagnetic material, and have four arm portions intersecting one another at right angles. Plate member 30 is located above the support base 26, and can be moved in the x- and y-directions by means of the hollow flexible pillar 31. The top portion of the pillar 31 is connected to the center of member 30 and the lower portion is supported by base 26. The flexible pillar 31, which is, for example, a stainless-steel tube, is capable of elastic deformation. Each end of the arm portion of the movable member 30 has a coil 33, which includes a bobbin 32, formed of nonmagnetic material such as aluminum. The coil 33 is formed by a covered copper wire wound around the bobbin 32. Thus, two pairs of coils 33 (only one pair for the x-direction is shown in FIG. 2) are arranged individually at symmetrical positions in the x- and y-direction, with respect the acoustic lens 27. Square or U-shaped yokes 34 are disposed on the support base 26, corresponding to the coils 33. Two pairs of permanent magnets 35a, 35b and 36a, 36b are fixed to each yoke 34, opposing each other across coil 33. In this arrangement, magnetic fluxes of opposite directions pass at the opposite side portions with respect to the driving direction.

Thus, in the present embodiment, when a required current is supplied to one of the coils 33 in each pair, it cooperates with the magnetic fluxes of the permanent magnets 35a, 35b, 36a and 36b, thus performing an electromagnetic action. This action causes the movable member 30 to drive the acoustic lens 27 two-dimensionally in the x- and y-directions. In this manner, the sample 11 is two-dimensionally scanned with an ultrasonic beam emitted from the lens 27, and the region for the scanning, i.e., the field of view, is selected. When the other of the coils 33 in each pair is moved, a current is caused to flow through it by an electromotive force. By detecting this current, therefore, the moving speed of the acoustic lens 27 can be monitored. A coaxial cable 37 is connected to the lens 27 at one end. The cable 37 passes through the flexible pillar 31 and extends to the outside through the side wall portion of the adiabatic vessel 4, or the opening 3a of the base plate 3, and a sealing device. The other end of the cable 37 is connected to a signal processing circuit. The lead wire of each coil 33 is also led to the outside through the sealing device, and connected to a driver circuit.

A piezoelectric actuator 100 is connected between the acoustic lens 27 and the movable member 30. This actuator 100 is designed to expand and contract in the z-direction according to input signals, thereby to move the lens 27 in the z-direction and to achieve focusing. The operator of the ultrasonic microscope rotates the spindle of the micrometer 13a, while looking at the reflection waveform output by the microscope and monitored by a known display. As a result, the sample rod 10 is moved in the z-direction, whereby a coarse focusing is performed. After performing the coarse focusing, the operator then operates the piezoelectric actuator 100, thereby effecting a minute focusing.

The piezoelectric actuator 100 can be designed to expand and contract for a relatively long distance. If this is the case, the microscope does not require the micrometer 13a, and both the coarse focusing and the minute focusing can be accomplished by the actuator 100 only.

The amplitude of the signal output from the acoustic lens 27 is displayed by an external monitor device, such as a CRT or a voltmeter. When the amplitude of the signal reaches the maximum value, it is understood that the ultrasonic beam is completely focused on the sample 11. Since the piezoelectric actuator 100 expands and contracts in accordance with the voltage applied to it, it is easy to achieve the focusing merely by changing that voltage.

FIGS. 3A and 3B illustrate the x-axis driver circuit and y-axis driver circuit, both incorporated in the X-Y scanner 50, for driving the acoustic lens 27 in the x- and y-directions, respectively. In the x-axis driver circuit shown in FIG. 3A, the output of a sinewave generator 40 is supplied to one input of an adder 42 through an attenuator 41 for adjusting the amplitude of the output of generator 40. A voltage Vx is applied from a variable voltage source 43 to the other input of the adder 42, and the output of the adder 42 is supplied to the x-axis drive coil 33 through a power amplifier 44. In the y-axis driver circuit shown in FIG. 3B, the output of a sawtooth-signal generator 45 is supplied to one input of an adder 47 through an attenuator 46. A voltage Vy is applied from a variable voltage source 48 to the other input of adder 47, and the output of the adder 47 is supplied to a y-axis drive coil 33 through a power amplifier 49. The outputs of the generators 40 and 45 are synchronized so that the acoustic lens 27 can be moved two-dimensionally, in the x- and y-directions.

The acoustic lens 27 is moved for a distance corresponding to the output voltage Vx of the variable voltage source 43, in the x-direction, by means of the flexible pillar 31, and undergoes sine-oscillation around the reached position in response to a sine-wave signal. In the y-direction, the lens 27 is moved for a distance corresponding to the output voltage Vy of the variable voltage source 48 by means of the pillar 31, and undergoes a y-direction displacement from to the reached position. Thus, the sample 11 is two-dimensionally scanned, in the x- and y-directions, within ranges corresponding to the outputs of the attenuators 41 and 46, starting at positions corresponding to the voltages Vx and Vy. Accordingly, the field of view can be automatically selected as required by adjusting the output voltages Vx and Vy of the voltage sources 43 and 48. Moreover, the displacement of the acoustic lens 27, if occurring during this field selection, is attributable only to the elastic deformation of the flexible pillar 31 which supports the lens. Therefore, the field of view can be selected with high accuracy and reproducibility. Since the field of view can be selected electrically, furthermore, the operating efficiency is high enough to permit computer control with ease.

Figure 4:
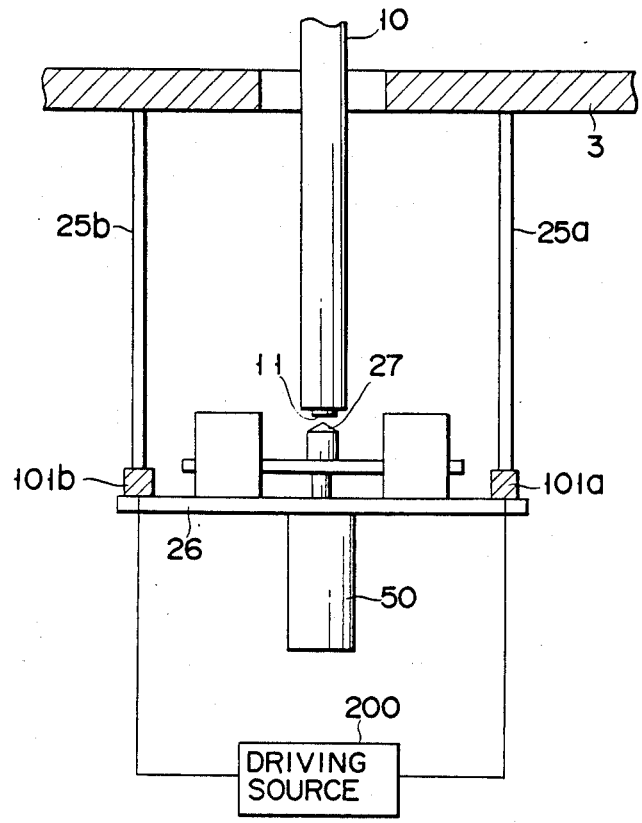
FIG. 4 is a schematic view illustrating an ultrasonic microscope according to a second embodiment of the invention.
Figure 5A:
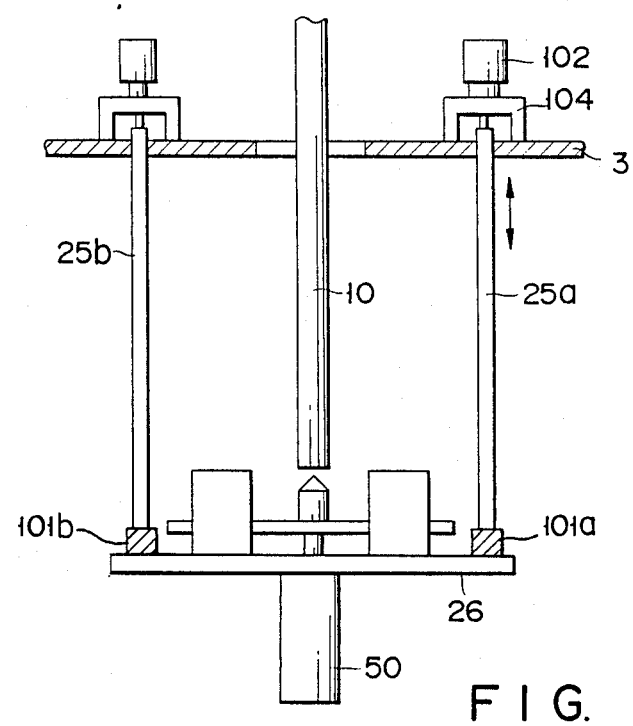
FIG. 5A is a schematic view showing another ultrasonic microscope which is a third embodiment of the invention.
Figure 5B:
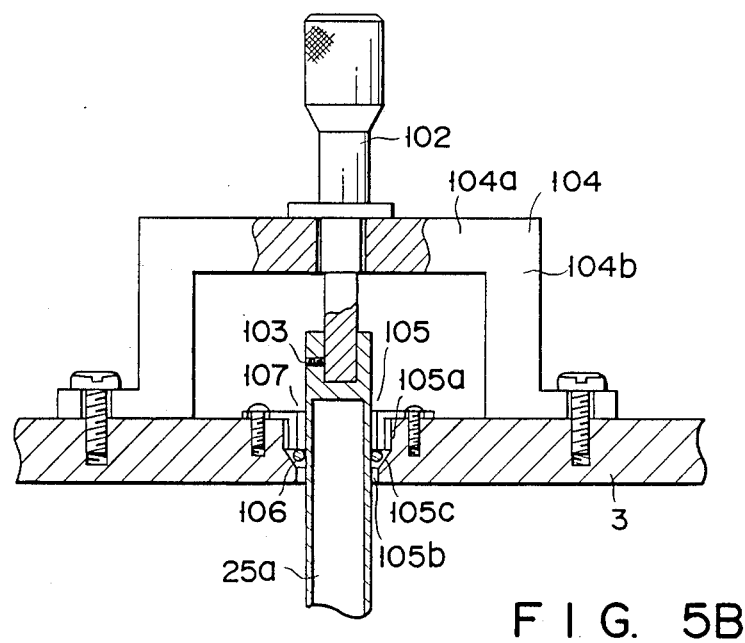
FIG. 5B is an enlarged view illustrating a part of the third embodiment shown in FIG. 5A.

FIG. 4 shows the second embodiment of the invention. This embodiment has two stays 25a, 25b, and two piezoelectric actuators 101a and 101b, both designed to expand and contract in the z-direction. The first actuator 101a is located between a support base 26 and stay 25a. Similarly, the second actuator 101b is located between the base 26 and stay 25b. When an electrical signal is supplied by a signal generator (not shown) to these actuators 101a and 101b, both actuators 101a and 101b expand or contract, thereby moving an X-Y scanner 50 up or down. As a result, the distance between an acoustic lens 27 and a sample 11 attached to the lower end of a sample rod 10 may be regulated. The sample rod 10 can be coarsely moved in the z-direction by means of a micrometer 13a, or need not be moved at all in the z-direction. Alternatively, four stay-actuator units can be mounted on the support base 26 and positioned around the sample rod 10, spaced apart at angular intervals of about 90°. In this case, the X-Y plane can be tilted in any desired direction when different voltages are applied to the four piezoelectric actuators from a driving source 200. FIGS. 5A and 5B illustrate the third embodiment of the present invention. The X-Y scanner 50 of this embodiment can be moved up and down as in the second embodiment (FIG. 4). A support base 26 supporting the scanner 50 is suspended from a base plate 3 by means of at least two stays 25a and 25b.

As is shown in FIG. 5B, the upper end portion of either stay protrudes upward from the plate 3, passing through a through hole 105 formed in the plate 3. The hole 105 includes an upper, large-diameter portion 105a and a lower, small-diameter portion 105b, and a tapered portion 105c connecting the portions 105a and 105b. An O-ring 106 is fitted in the tapered portion 105c, thus sealing the upper and lower portions 105a and 105b from each other in airtight fashion. A cap 107 closes the upper, large-diameter portion 105a of the hole 105. The cap 107 is fastened to the plate 3 by screws downwardly, depressing the O-ring 106 within the tapered portion 105c of the hole 105. Hence, a vacuum seal is provided between the hole 105 and the upper end portion of the stay 25a.

Also, as is illustrated in FIG. 5B, the upper end of either stay is fastened to the lower end of a micrometer head 102 by a screw 103. The upper end of the micrometer head 102 is attached to the top plate 104a of a micrometer base 104 and positioned coaxial with the stay. The micrometer base 104 has legs 104b which are secured to the base plate 3 by means of screws.

When the spindles of the micrometers are rotated, the stays 25a and 25b, which are connected to the base 26 are moved up or down in accordance with the direction of rotating the spindles. As a result, the support base 26 is moved up or down, and the X-Y scanner 50 is vertically moved to perform focusing. As is shown in FIG. 5A, a sample rod 10 extends vertically, passing through a hole formed in the base plate 3. This rod 10 is of the same structure as its counterparts used in the first embodiment (FIG. 1) and the second embodiment (FIG. 4). The second and third embodiments have at least two mechanisms which may operate independently of each other, for moving the support base 26 in the vertical direction. Therefore, these mechanisms cooperate to tilt the X-Y scanner 50, whereby to the two-dimensional scanning surface of the acoustic lens 27 can be positioned parallel to the surface of the sample 11. More specifically, the X-Y scanner 50 is moved in the x-direction and the y-direction, then the values are detected which a voltage signal has when the sample 11 is set at several positions, and then the mechanisms are operated, thus moving the base 26 vertically, until these values become substantially equal, indicating that the scanning surface of the lens 27 has been located substantially parallel to the surface of the sample 11.

What is claimed is:

1. An ultrasonic microscope comprising:
   an acoustic lens for applying an ultrasonic beam to a sample;
   first supporting means for supporting said acoustic lens;
   second supporting means for supporting said sample to set the sample opposite to said acoustic lens;
   drive means for moving said acoustic lens in one direction so that the distance between said acoustic lens and the sample varies by moving said first supporting means; and
   means for containing cryogenic liquid used as an ultrasonic transmission medium, in which said acoustic lens and sample are immersed;
   said first supporting means including:
   scanning means for causing said acoustic lens to scan the sample two-dimensionally in a plane perpendicular to said one direction;
   a support base for supporting said drive means; and
   at least two stays supporting said base at points different from each other and being movable in said one direction;
   said drive means being coupled to said at least two stays so as to adjust a moving amount of each stay independently, said drive means including adjust means for adjusting the slope of said lens with respect to the sample.

2. The ultrasonic microscope according to claim 1, wherein said drive means comprises piezoelectric means which expands and contracts when a voltage is applied to said piezoelectric means, thereby to change the distance between the sample and said acoustic lens.

3. The ultrasonic microscope according to claim 2, wherein said scanning means comprises a plate-like member capable of moving in a plane perpendicular to said one direction in which said acoustic lens is moved by said piezoelectric means.

4. The ultrasonic microsconic microscope according to claim 2, wherein said piezoelectric mean comprises piezoelectric actuators respectively provided between said support base and each of said stays.

5. The ultrasonic microscope according to claim 4, further comprising a driving source electrically connected to said piezoelectric actuators, and means for applying different voltages from said driving source to said piezoelectric actuators, thereby to drive and control said piezoelectric actuators.

6. The ultrasonic microscope according to claim 1, further comprising means connected to said second support means, for coarsely moving said second support means.

7. The ultrasonic microscope according to claim 6, wherein said means for coarsely moving said second support means comprises slope adjust means for adjusting said sample in a plane perpendicular to said one direction.

8. The ultrasonic microscope according to claim 1, wherein said adjust means comprises a micrometer heat which is manually operated to change the distance between said acoustic lens and the sample.

9. The ultrasonic microscope according to claim 8, wherein said first support means has drive means for moving said acoustic lens in two directions in a plane perpendicular to each other, thereby to cause said acoustic lens to scan the sample, a support base supporting said drive means, and at least two stays extending vertically and supporting said support base, and a base plate supporting said at least two stays and having a hole allowing the passage of said second support means.

10. The ultrasonic microscope according to claim 9, wherein said base plate has at least two through holes allowing the passage of said stays, respectively, each hole having an upper, large-diameter portion, a lower, small-diameter portion, and a tapered portion connecting the upper and lower portions, and said first support means has O-rings and screws connecting said stays to said micrometer head, each of said O-rings fitted in the tapered portion of said through hole and mounted on said stay passing through said hole, thus providing a seal between said through hole and said stay.

11. The ultrasonic microscope according to claim 1, wherein said means for containing said cryogenic liquid includes:
a housing maintaining airtightness with respect to the atmosphere, and comprising a transparent plate; and
a cover covering said housing in a vacuum state, and having a transparent plate.

12. The ultrasonic microscope according to claim 1, wherein said driving means comprises:
high-speed drive circuit means for generating a sine wave;
low-speed drive circuit means for generating a saw tooth wave;
high-speed drive coil means for driving said acoustic lens in a high-speed scan direction upon receiving said sine wave;
low-speed drive coil means for driving said acoustic lens in a low-speed scanning direction upon receiving said saw tooth wave; and
variable voltage source means for adding adjustable DC components to said sine wave and to said saw tooth wave, thereby selecting the field of said acoustic lens.

13. An ultrasonic microscope comprising:
a main body;
an acoustic lens for applying an ultrasonic wave toward a sample and for receiving an ultrasonic wave beam reflected from the sample;
a support base for supporting said acoustic lens;
at least two stays, arranged in parallel and movable in the vertical direction, having upper portions and lower portions, said lower portions supporting said support base at different points and said upper portions supporting said main body;
means for supporting a sample so that the sample opposes said acoustic lens;
moving means for moving said acoustic lens in a vetrtical direction so that a distance between the sample and said acoustic lens varies;
means for containing an ultrasonic transmission medium in which said acoustic lens and sample are immersed; and
scan means for causing said acoustic lens to scan the sample two-dimensionally in a horizontal direction;
said drive means having piezoelectric actuators provided between said a t least two stays and said support base.

14. An ultrasonic microscope comprising:
containing means for containing a cryogenic liquid used as an ultrasonic transmission medium, said containing means being sealed from the outside atmosphere and having a sealable opening therethrough;
an acoustic lens;
first support means for supporting said lens in said cryogenic liquid;
second support means comprising a sample rod for removably supporting a sample in said cryogenic liquid, said sample rod passing through said sealable opening;
said first support means comprising a support base and at least two stays extending from said support base to said containing means; and
drive means or moving said acoustic lens in a vertical direction to change a distance between said acoustic lens and said sample.

15. The ultrasonic microscope according to claim 14 wherein said drive means comprises piezoelectric means between said support base and said acoustic lens.

16. The ultrasonic microscope according to claim 14 further comprising means external of said containing means for moving said sample rod to coarsely adjust the distance between said acoustic lens and said sample.

17. The ultrasonic microscope according to claim 14 wherein said first support means comprises scanning means for moving said acoustic scanning means for moving said acoustic lens two dimensionally in a scanning plane at least substantially perpendicular to said vertical direction.

18. The ultrasonic microscope according to claim 17 wherein said drive means comprises at least two piezoelectric actuators interposed between respective said stays and said support base.

19. The ultrasonic microscope according to claim 18 wherein said piezoelectric actuators are independently driven, whereby the tilt of said scanning plane may be adjusted.

20. The ultrasonic microscope according to claim 17 further comprising means external of said containing means for independently moving said stays vertically to coarsely adjust the distance between said acoustic leans and said sample and to coarsely adjust the tilt of said scanning plane.

* * * * *